United States Patent [19]

Boissinot et al.

[11] Patent Number: 4,666,478
[45] Date of Patent: May 19, 1987

[54] SCRUBBER APPARATUS FOR PURIFYING FOUL AIR PRODUCED DURING AN EMBALMING, AN AUTOPSY OR THE LIKE

[75] Inventors: Jean-Guy Boissinot, Loretteville; Pierre Begin, Levis, both of Canada

[73] Assignee: E.F.C. Control Inc., Beauport, Canada

[21] Appl. No.: 788,112

[22] Filed: Oct. 16, 1985

Related U.S. Application Data

[63] Continuation-in-part of Ser. No. 661,919, Oct. 17, 1984, Pat. No. 4,553,992.

[30] Foreign Application Priority Data

Oct. 23, 1984 [CA] Canada .................... 466132

[51] Int. Cl.$^4$ .............................................. B01D 39/00
[52] U.S. Cl. ......................................... 55/279; 55/316; 55/470; 55/524; 98/115.1; 98/115.3; 126/299 D; 422/121
[58] Field of Search ................. 55/279, 467, 475, 471, 55/472, 497, 498, 500, 521, 524, 316; 126/299 D; 98/115.1, 115.3; 422/4, 5, 24, 121; 27/1, 23; 128/1 R, 139

[56] References Cited

U.S. PATENT DOCUMENTS

| | | | |
|---|---|---|---|
| 3,125,869 | 3/1964 | Winton ........................ | 98/115.1 X |
| 3,511,162 | 5/1970 | Truhan ........................ | 55/279 X |
| 3,570,222 | 3/1971 | Dudek et al. ................ | 55/472 |
| 3,744,216 | 7/1973 | Halloran ..................... | 55/102 |
| 3,798,879 | 3/1974 | Schmidt-Burbach et al. ....... | 55/102 |
| 3,844,741 | 10/1974 | Dimitrik ..................... | 55/102 |
| 3,846,072 | 11/1974 | Patterson ................... | 21/74 R |
| 3,925,021 | 12/1975 | Yoshino et al. .............. | 55/524 X |
| 4,102,654 | 7/1978 | Pellin ........................ | 55/102 |
| 4,118,191 | 10/1978 | Böhnensieker ................ | 55/279 |
| 4,140,105 | 2/1979 | Duvlis ....................... | 128/1 R |
| 4,233,044 | 11/1980 | Allan ........................ | 55/355 |
| 4,252,547 | 2/1981 | Johnson ..................... | 55/234 |
| 4,268,282 | 5/1981 | MacKenzie .................. | 55/498 X |
| 4,333,745 | 6/1982 | Zeanwick .................... | 55/472 X |
| 4,333,750 | 6/1982 | Helmus ...................... | 55/473 X |

OTHER PUBLICATIONS

I & E C Product Research and Development, vol. 4, Mar. 1965, pp. 48–50.

Primary Examiner—Charles Hart
Attorney, Agent, or Firm—Schwartz, Jeffery, Schwaab, Mack, Blumenthal & Evans

[57] ABSTRACT

An air scrubber apparatus which purifies foul air produced during an embalming, an autopsy or the like carried out on a work table disposed in a room. This scrubber apparatus comprises a housing positioned above the work table and defining a central compartment provided with a bottom opening, and first and second longitudinal, side compartments adjacent the central compartment and provided with end outlets to the room. An air filter is positioned over the bottom opening of the central compartment and comprises a filtering material including aluminium oxide and potassium permanganate. First and second fans move the foul air towards the interior of the central compartment through the air filter for the purpose of purifying this foul air. The first fan also transfers the purified air from the central compartment to the first outer compartment while the second fan transfers it from the central compartment to the second outer compartment, to thereby disperse the purified air in the room through the end outlets of the outer compartments. At least one ultraviolet ray tube or an additional filter may also be provided to kill germs, bacteria and the like present in the moved foul air. In order to increase the efficiency of the scrubber apparatus, a wall structure may define a substantially closed volume between the housing and the work table.

17 Claims, 11 Drawing Figures

SCRUBBER APPARATUS FOR PURIFYING FOUL AIR PRODUCED DURING AN EMBALMING, AN AUTOPSY OR THE LIKE

CROSS-REFERENCE

This application is a continuation-in-part of application Ser. No. 661,919, filed Oct. 17, 1984 now U.S. Pat. No. 4,553,992.

BACKGROUND OF THE INVENTION

1. Field of the Invention

The present invention relates to an air scrubber apparatus designed for purifying foul air produced during, for example, an embalming or an autopsy carried out on a work table in an embalming or autopsy room.

It should be pointed out that the use of the scrubber apparatus of the invention is not limited to its use for embalming and autopsy. Indeed, it can be used for any other purpose provided that malodorous, pungent and/or corrosive gaseous substances similar to those inherent to embalming and autopsy or which can be removed by air filter means of the scrubber apparatus of the invention are mixed to the ambient air, thereby rendering necessary a cleaning of the ambient air from such gaseous substances in order to keep breathable the air in the room.

2. Related Art

In conventional autopsy or embalming rooms, exhaust fans are provided to evacuate the produced foul air to the outside. An important drawback of such exhaust fans is that, while evacuating to the outside the foul air, heated or cooled air is also evacuated thereby greatly increasing the heating and conditioning costs.

A solution to this drawback is to use an air scrubber apparatus which returns the air to the room after purification thereof. Some apparatuses of this type are proposed for example in U.S. Pat. Nos. 3,844,741 (Dimitrik), 3,846,072 (Patterson), 4,118,191 (Bohnensieker), and 4,252,547 (Johnson). However, none of these apparatuses is adapted for its use in a room to carry out, for example, embalming or autopsy

OBJECTS AND SUMMARY OF THE INVENTION

An object of the present invention is therefore to provide an air scrubber apparatus which may be used in association with a work table in an embalming or autopsy room, and which eliminates the above-mentioned drawback of the conventional exhaust fans.

More specifically, according to the present invention, there is provided an air scrubber apparatus for purifying foul air produced during an embalming, an autopsy or the like carried out on a work table disposed in a room for embalming, autopsy or the like, comprising:

a housing positioned above the work table, said housing defining a first compartment provided with bottom inlet opening means for said foul air, and a second compartment adjacent to said first compartment and provided with outlets to said room which are located at predetermined positions;

first air filter means positioned over said bottom inlet opening means of the first compartment, said first filter means comprising a filtering material including aluminium oxide and potassium permanganate and being designed to allow passage of air through it, said filtering material which includes aluminium oxide and potassiun permanganate purifying said foul air upon passage thereof through said first filter means; and air pumping means for moving said foul air towards the interior of said first compartment through said first filter means for the purpose of purifying said foul air, said pumping means comprising means for transferring the purified air from the first compartment to said second compartment in order to return the purified air to said room through said outlets, said predetermined positions of said outlets of the second compartment being selected so as to enable a dispersion of the purified air in said room.

Also in accordance with the present invention, there is provided an air scrubber apparatus for purifying foul air produced during an embalming, an autopsy or the like carried out on a work table disposed in a room for embalming, autopsy or the like, comprising:

a housing positioned above the work table, this housing defining a first outer compartment and a second outer compartment disposed substantially horizontally with respect to each other, the housing also defining a central compartment disposed between the first and second outer compartments, this central compartment being provided with bottom inlet opening means for the foul air, and the first and second outer compartments being each provided with outlets to the room which are located at predetermined positions;

air filter means positioned over the bottom inlet opening means of the central compartment, these filter means comprising a filtering material including aluminium oxide and potassium permanganate and being designed to allow passage of air through it, the filtering material which includes aluminium oxide and potassium permanganate purifying the foul air upon passage thereof through the filter means; and air pumping means for moving the foul air towards the interior of the central compartment through the filter means for the purpose of purifying this foul air, such pumping means comprising means for transferring the purified air from the central compartment to the first and second outer compartments in order to return the purified air to the room through the outlets of these first and second outer compartments, the predetermined positions of these outlets being selected so as to enable a dispersion of the purified air in the room.

Preferably, the air scrubber apparatus according to the present invention comprises means for killing germs, bacteria and the like present in the moved foul air. These killing means may take the form of at least one ultraviolet ray tube or the form of additional filter means.

BRIEF DESCRIPTION OF THE DRAWINGS

The objects, advantages and other features of the present invention will become more apparent upon reading of the following non restrictive description of preferred embodiments thereof, made with reference to the accompanying drawings in which.

DETAILED DESCRIPTION OF THE INVENTION

Figure 4:
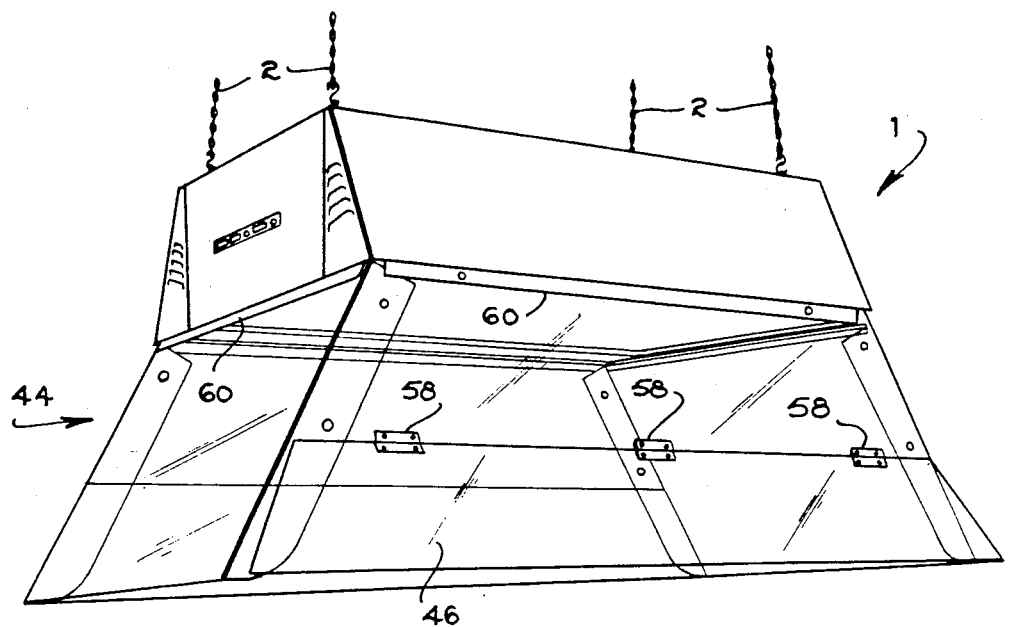
FIGS. 4 and 5 illustrate the air scrubber apparatus of FIG. 1 provided with four adjustable chain hangers for hanging up the housing thereof from the ceiling of the room, and with plexiglass panels thereunder which surround a volume located between the housing of the scrubber apparatus and the top surface of the work table.
Figure 5:
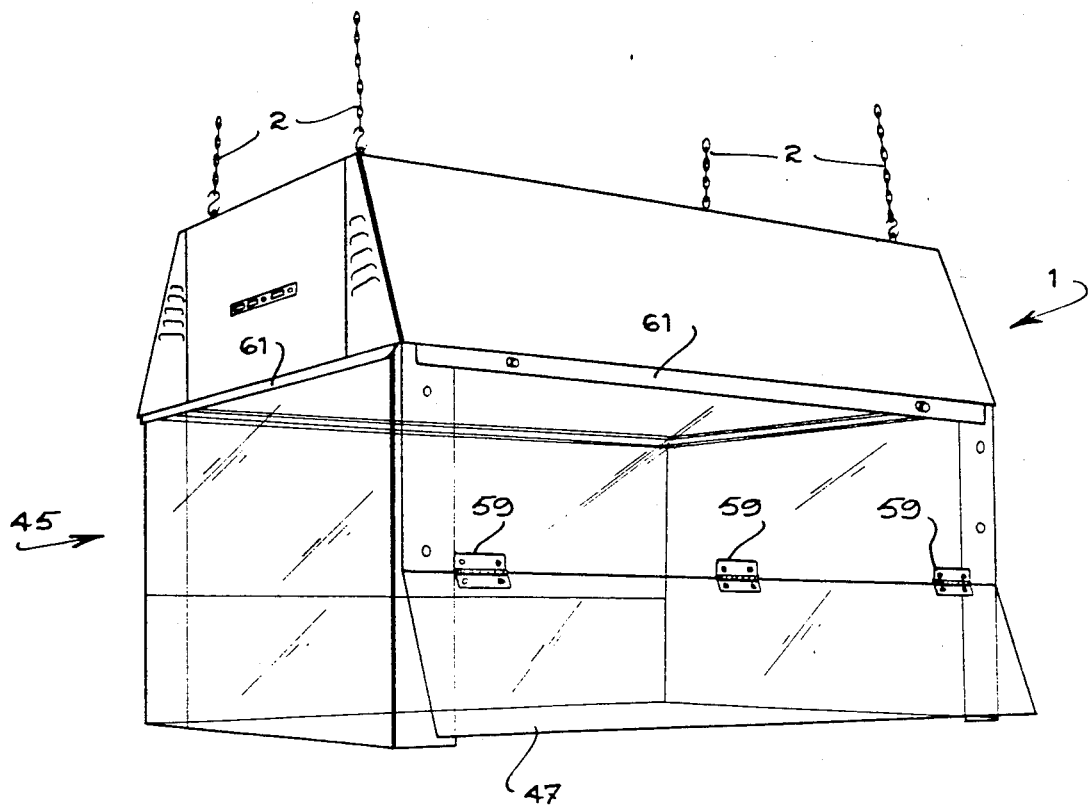

As illustrated on FIGS. 4 and 5 of the drawings the air scrubber apparatus comprises a housing designated generally by the reference numeral 1 which is hung up from the ceiling of for example an embalming or autopsy room above a work table disposed in this room by means of four adjustable chain hangers 2 attached respectively to one corner of a top surface 3 (see FIG. 6) of the housing 1.

Figure 1:
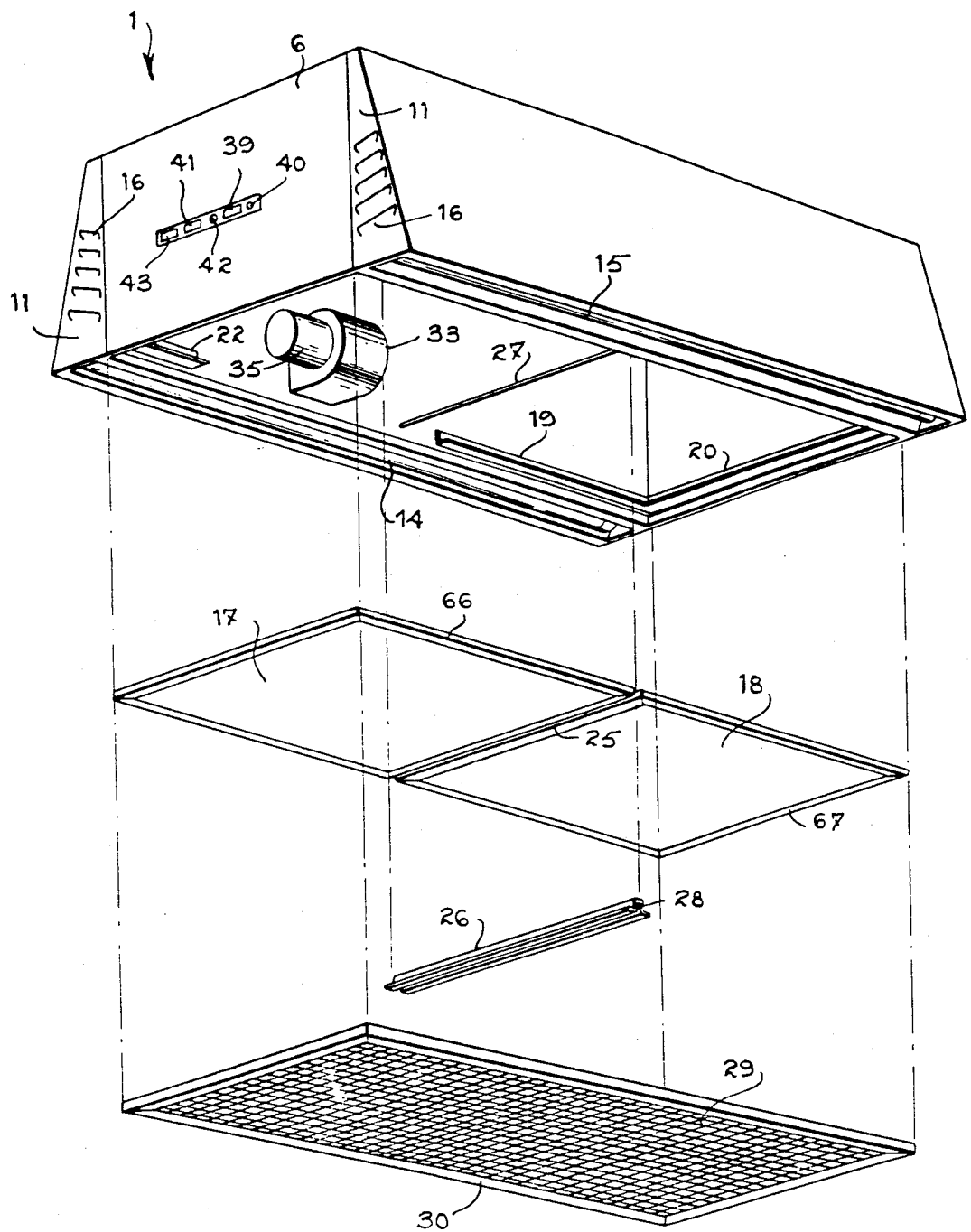
FIG. 1 is an explosion view of a first embodiment of the air scrubber apparatus according to the invention.
Figure 2:
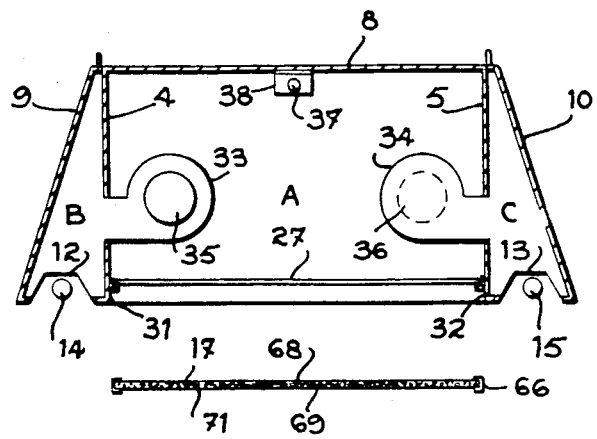
FIG. 2 is a cross sectional view of the air scrubber apparatus of FIG. 1.
Figure 3:
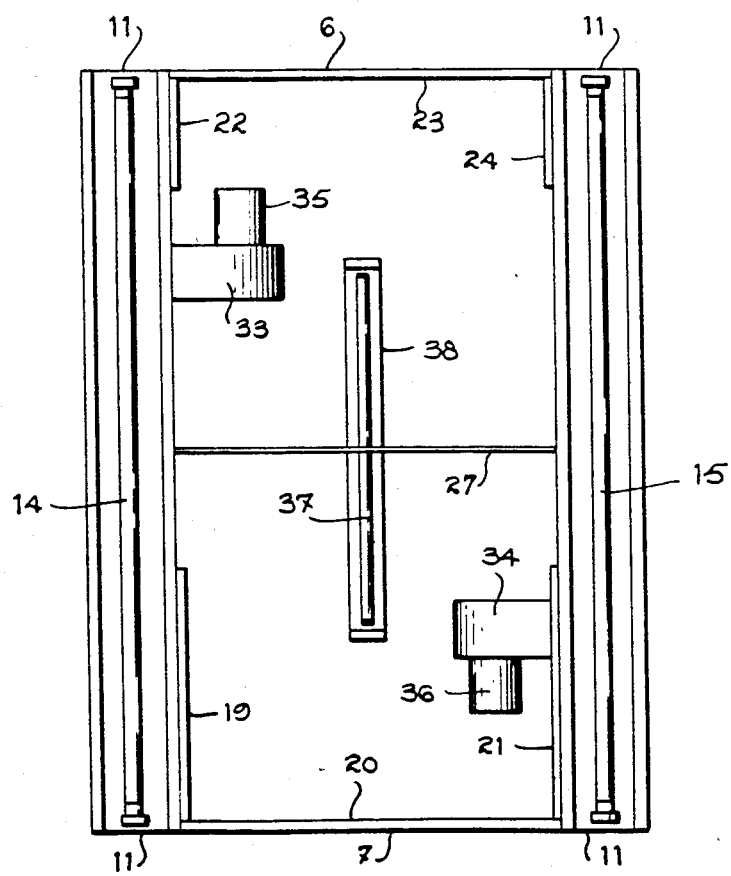
FIG. 3 is a bottom view of the air scrubber apparatus of FIG. 1.

Referring now to FIGS. 1 to 3 of the drawings, the housing designated generally by the reference numeral 1 is made of sheet material, for example stainless steel or aluminium. The housing 1 comprises a top wall 8, two inner side walls 4 and 5 and two end walls 6 and 7 defining a central compartment A. The housing 1 also comprises two outer side walls 9 and 10 which are formed as shown on FIGS. 1 and 2 and which define with the inner side walls 4 and 5, with four end walls 11 each located at a corresponding corner of the housing 1, and with bottom walls 12 and 13 a first longitudinal outer compartment B and a second longitudinal outer compartment C.

The bottom walls 12 and 13 constitute respectively a receptacle and reflector for cold white fluorescent tubes 14 and 15, which tubes provide sufficiently with light the top surface of the corresponding work table. As can be seen, the tube 14 is mounted under the first compartment B and the tube 15 is mounted under the second outer compartment C.

As shown on FIG. 1, the four end walls 11 are each provided with outlets to the room such as 16.

The bottom wall of the central compartment A is formed by two filter portions 17 and 18 each forming one half of such a bottom wall. For mounting these filter portions 17 and 18, metal supports 19, 20, 21, 22, 23 and 24 each formed aith a 90° angle are fixed to the housing 1 as shown on FIGS. 1 to 3. As can be deduced from these three Figures, the following procedure may be followed to mount the portions 17 and 18. In a first step, the filter portion 18 is positioned on the supports 19, 20, and 21. In a second step, the end 25 of this portion 18 is lifted to allow positioning of an holding part 26 so that a groove 28 of this holding part 26 is positioned on a rod 27 mounted transversally between the inner side walls 4 and 5, the rod 27 thereby maintaining in place the part 26. Thereafter the end 25 is released. In a last step, the filter portion 17 is introduced in the central compartment A and positioned on the supports 22, 23 and 24 and on the holding part 26. The structure of the filter portions 17 and 18 will be further elaborated hereinafter.

A metal mesh 29 provided with a frame 30 is mounted under the filter portions 17 and 18 and held in place by adjustment between the lower parts of the walls 4, 5, 6 and 7 below the supports 19 to 24 such as 31 and 32.

In operation, two fans 33 and 34 when driven through corresponding electrical motors 35 and 36, respectively, move the foul air, produced during for example an embalming or an autopsy carried out on the work table located under the housing 1, towards the interior of the central compartment A through the metal mesh 29 and the filter portions 17 and 18 for the purpose of purifying the moved foul air.

An ultraviolet "black light" fluorescent tube 37 is mounted inside the compartment A on the top wall 8 through an holding assembly 38 to kill through its ultraviolet radiation germs, bacteria and the like present in the purified air in the central compartment A, which germs, bacteria and the like are therefore present in the foul air moved inside this compartment A.

The fan 33 transfers a first part of the purified air from the central compartment A to the first outer compartment B for a dispersion thereof in the room through the end outlets 16 of the compartments B, and the fan 34 transfers a second part of the purified air from the central compartment A to the second outer compartment C for a dispersion thereof in the room through the end outlets 16 of the compartment C.

As illustrated on FIG. 3 and for a proper operation of the scrubber apparatus, the fan 33 is located in a first half of the central compartment A while the fan 34 is located in the second half of this compartment A, thereby producing passage of foul air through the entire surface of the filter portions 17 and 18.

FIG. 1 shows a first switch 43 provided to energize the two fluorescent tubes 14 and 15, a second switch 41 with its associated indicating lamp 42 provided to energize the ultraviolet fluorescent tube 37, and a third switch 39 with its associated indicating lamp 40 provided to energize the two motors 35 and 36. Of course, the three fluorescent tubes 14, 15 and 37 are energized through corresponding ballasts which are not shown on the different Figures of the attached drawings.

As shown on FIGS. 4 and 5, the volume located between the housing 1 and the top surface of the work table disposed thereunder may be closed through a plexiglass panel structure 44 or 45 appropriately fixed to the housing 1 through parts 60 or 61 to reduce dispersion into the room of the malodorous, pungent and/or corrosive gaseous substances produced during, for example an embalming or an autopsy carried out on the work table. The panels of the structure (44 or 45) may be inclined (see 44 on FIG. 4) or vertical (see 45 on FIG. 5) depending on the dimensions of the top surface of the work table with respect to those of the housing 1. In both cases, the plexiglass panel structure is provided with a panel such as 46 or 47 preferably on each side of the work table, this panel 46 or 47 being fixed at its upper side to the remainder of the structure 44 or 45 through hinges 58 or 59, for the purpose of allowing access to the interior of the plexiglass structure 44 or 45 and consequently to the top surface of the work table. The plexiglass panel structure 44 or 45 therefore increases the efficiency of the scrubber apparatus, when used with bad smelly cases and for contagious cases, etc., by allowing working in a bacteria free environment and with no bad odors.

Figure 6:
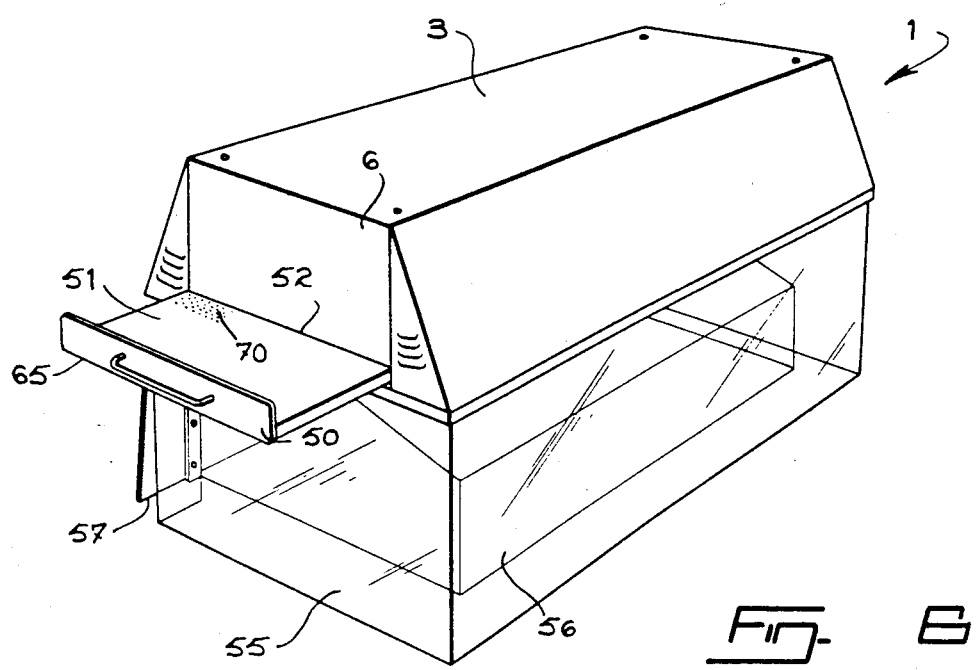
FIGS. 6 and 7 show a second embodiment of the air scrubber apparatus of the invention differing from the first embodiment by the position of the means for killing germs, bacteria and the like present in the moved foul air, and by the structure of the purifying filter means, this second embodiment being provided with a plexiglass wall structure thereunder defining two distinct volumes in communication with each other in the proximity of the top surface of the work table.
Figure 7:
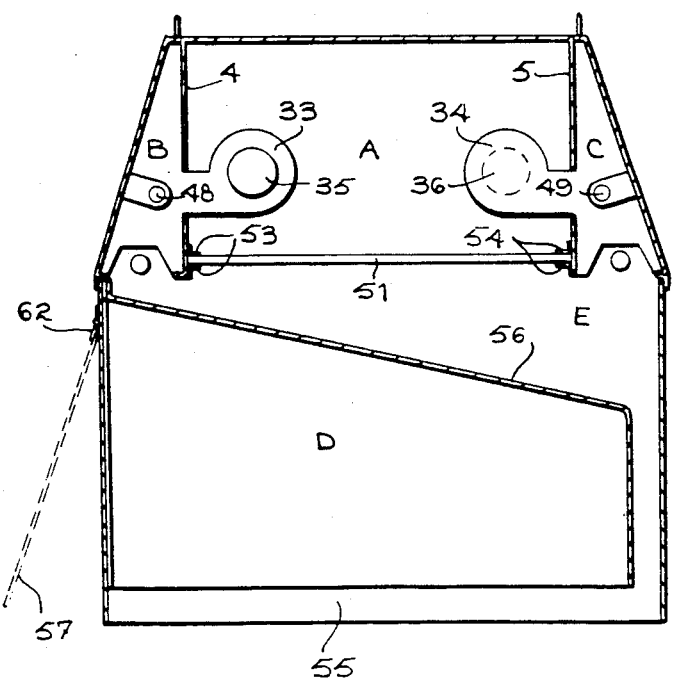

Referring now to FIGS. 6 and 7 of the drawings, the ultraviolet "black light" fluorescent tube 37 located in the central compartment A (see FIGS. 2 and 3) may be replaced by a first ultraviolet "black light" fluorescent tube 48 mounted in the first outer compartment B and a second ultraviolet "black light" fluorescent tube 49 mounted in the second outer compartment C. The two tubes 48 and 49 kill more efficiently the germs, bacteria and the like present in the purified air.

The scrubber apparatus of FIGS. 6 and 7 also comprises an air filter 65 comprising a filter portion 51 and a part 50 giving an external drawer-like shape to the air filter 65. For the purpose of positioning the filter portion 51, and end wall 6 has an opening 52 therein and guides 53 and 54 mounted on the inner side walls 4 and 5 are provided. Of course, the filter portion 51 replaces both the filter portions 17 and 18 of FIG. 1 and is positioned by sliding thereof in the guides 53 and 54 through the opening 52.

Of course, the metal mesh 29 of FIG. 1 can still be mounted by adjustment between the guides 53 and 54 in the same manner as described above.

The scrubber apparatus of FIGS. 6 and 7 further comprises an outer plexiglass panel structure 55 similar to the structure 45 of FIG. 5 and provided with a panel 57 fixed to the remainder of the structure 55 through hinges such as 62. An inner plexiglass panel structure 56 is also mounted inside the structure 55 around an opening open or closed through the panel 57, and defines a volume D in contact with the top surface of the work table and accessible through the opening corresponding to the panel 57. The inner structure 56 comprises three vertical panels having a lower end spaced from the work table thereby providing communication between the volume D and a volume E in contact with the filter portion 51. As can be seen, the only communication between on one hand the volume E, and on the other hand the volume D and the opening corresponding to the panel 57 is through the spacing between the top surface of the work table and the lower end of the vertical panels of the structure 56. When the fans 33 and 34 are in operation, it can be easily appreciated with reference to FIGS. 6 and 7 that the air in the volume D defined by the inner wall structure 56 is moved from this volume D to the filter portion 51 through the volume E and the spacing between the top surface of the work table and the lower end of the vertical panels of the inner structure 56. Such an inner structure 56 is particularly useful to move towards the filter portion 51 malodorous, pungent and/or corrosive gaseous substances heavier than the air.

Figure 8:
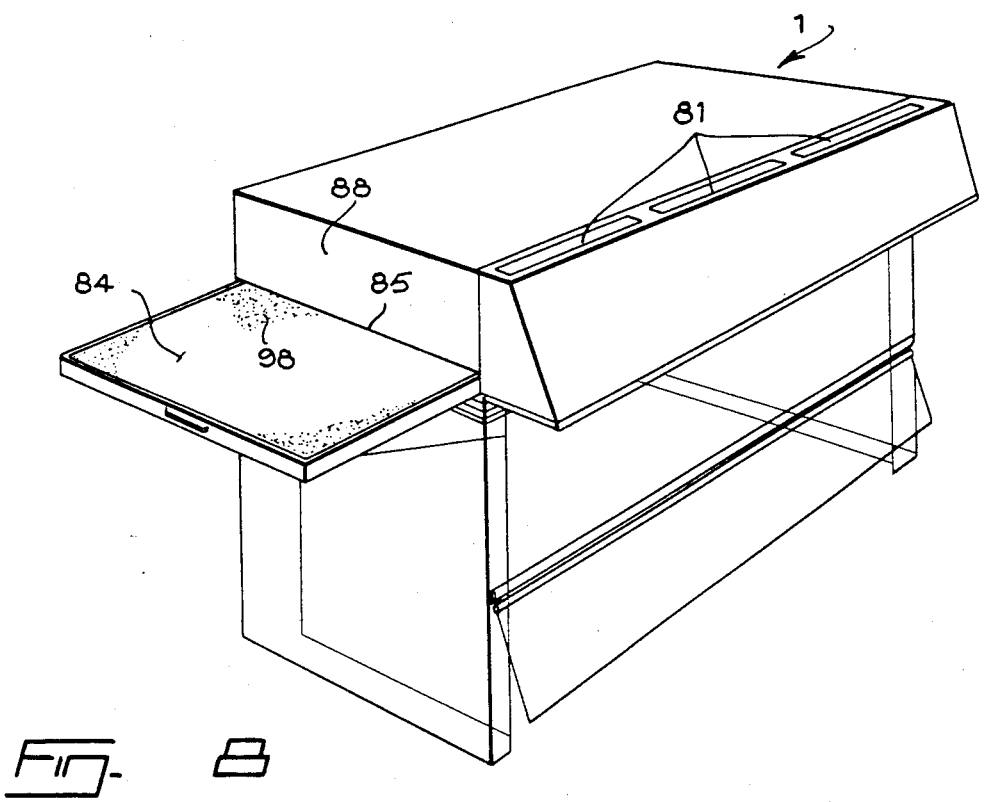
FIG. 8 illustrates a third embodiment of the air scrubber apparatus according to the invention.
Figure 9:
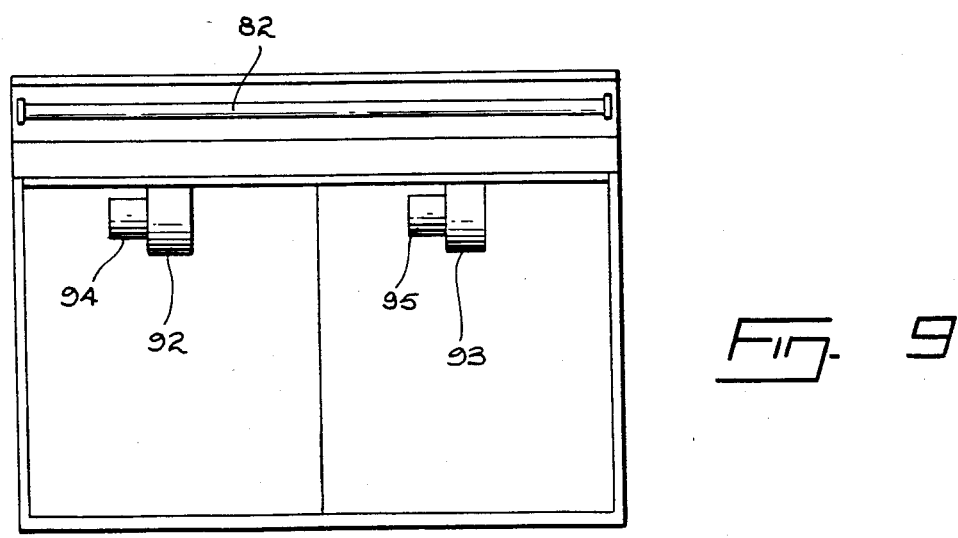
FIG. 9 is a bottom view of the housing of the air scrubber apparatus of FIG. 8.
Figure 10:
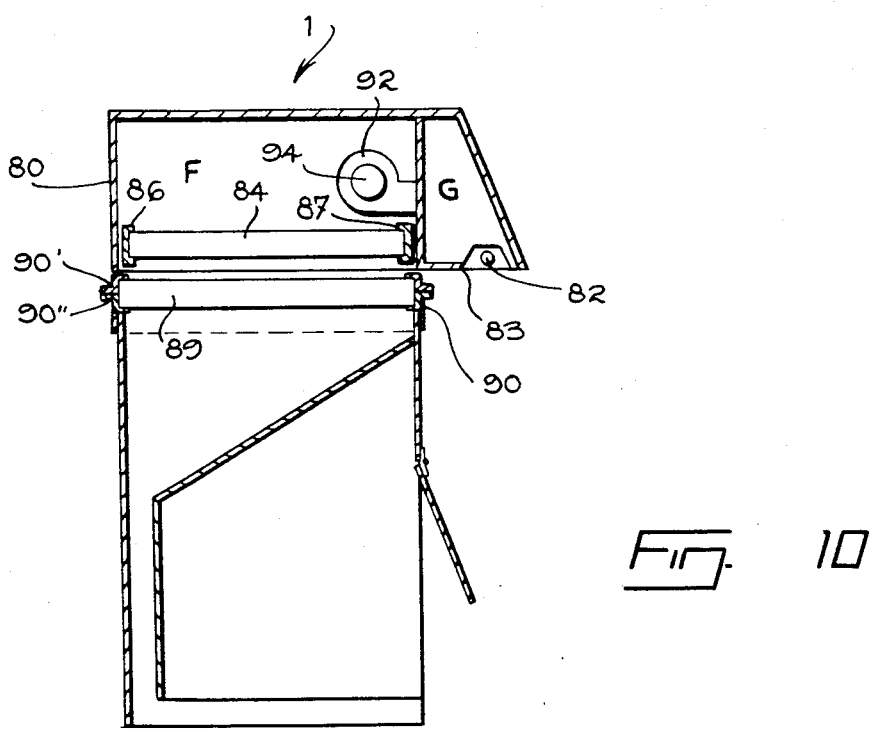
FIG. 10 is a cross sectional view of the air scrubber apparatus of FIG. 8.

FIGS. 8, 9 and 10 illustrate an embodiment of the scrubber apparatus according to the invention comprising a first compartment F and a second compartment G, which compartments F and G correspond respectively to the compartments A and C of the embodiment of FIGS. 1 to 3. Such an embodiment is particularly usefull for use in combination with a work table positioned close to a wall of the room in which this work table is located. Of course, the wall 80 (FIG. 10) of the housing 1 is in this case adjacent to the wall of the room.

As shown on FIG. 8, the compartment G is provided with upper outlets 81 to the room, and as shown on FIGS. 9 and 10, a cold white fluorescent tube 82 is mounted under this compartment G. Of course, the compartment G comprises a lower wall 83 (FIG. 10) forming a receptable and reflector for the fluorescent tube 82.

A filter portion 84 having a drawer-like structure can be positioned over the bottom inlet opening of the compartment F. Such a bottom inlet opening is formed by providing the compartment F with no bottom wall. More particularly, the filter portion 84 is positioned by sliding it in guides 86 and 87 through an opening 85 of an end wall 88 of the housing 1.

In the embodiment of FIGS. 8 to 10, the ultraviolet "black light" fluorescent tubes 37 (FIGS. 2 and 3) and 48 and 49 (FIG. 7) are replaced by an additional filter 89 superposed to the filter portion 84 and mounted through appropriate supports such as 90 which are fixed to the housing 1 for example by soldering. As illustrated on FIG. 10, the supports 90 are formed of two members 90' and 90" which can be for example screwed together so as to allow mounting and removal of the filter 89. The composition of the filter 89 is of course selected to kill efficiently germs, bacteria and the like. Advantageously, this filter 89 is constituted by a high efficiency particulate air filter (HEPA) which is formed with waterproofed, bactericidal and fungicidal treated paper folded into mini-pleats having a constant spacing between them. Due to the mini-pleat design, a maximum laminar flow effect is realized to ensure efficiency of the filter.

In operation, two fans 92 and 93 driven by associated electric motors 94 and 95 move the foul air towards the interior of the compartment F through the filter 89 to kill the germs, bacteria and the like presemnt in the moved foul air, and through the filter portion 84 to purify this moved foul air. The so treated air within the compartment F is thereafter transferred in the compartment G through the fans 92 and 93 for dispersion of this air in the room through the outlets 81.

As can be seen, the air scrubber apparatus of FIGS. 8 to 10 is provided with outer and inner plexiglass wall structures similar to that defined with reference to FIGS. 6 and 7, and fixed to the housing 1 through the members 90" of the supports 90.

Figure 11:
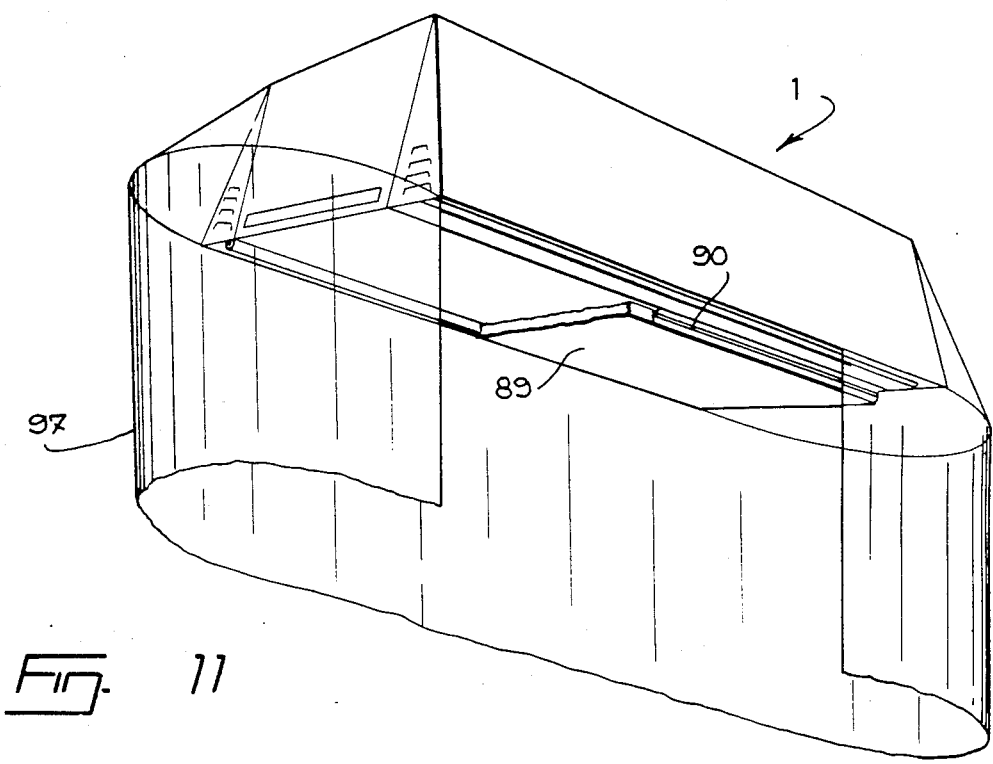
FIG. 11 shows an air scrubber apparatus according to the present invention provided with a transparent curtain suspended to the housing thereof.

Referring now to FIG. 11 of the attached drawings, the filter 89 and its associated supports 90 can be mounted on a scrubber apparatus as described with reference to FIGS. 1 to 3, in order to replace the ultraviolet fluorescent tube 37.

FIG. 11 also illustrates the possibility of providing a scrubber apparatus according to the present invention with a transparent curtain 97 suspended from the housing 1. Such a curtain 97 can be opened or closed by sliding it on appropriate track members through which it is suspended from the housing 1.

The structure of the filter portion 84 of FIGS. 8 and 10, of the filter portion 51 of FIGS. 6 and 7, and of the filter portions 17 and 18 of FIGS. 1 and 2 will now be described in details.

Each of these filter portions comprises a frame such as 66 and 67 (see FIGS. 1 and 2). Such a frame holds two sheets of for example polypropylene material such as 68 and 69 (see FIG. 2) provided with holes therein such as 70 (see FIG. 6) and 98 (see FIG. 8) to allow passage of air through them. The volume defined between the sheets 68 and 69 is filled with pellets such as 71 (see FIG. 2) of a filtering material, which sheets 68 and 69 are of course substantially rigid.

This filtering material is a mixture of two compounds: potassium permanganate and aluminium oxide. More particularly, the pellets of filtering material are activated pellets of aluminium oxide ($Al_2O_3$) which are impregnated with potassium permanganate ($KMnO_4$), and constitute a very effective agent to clean the air from malodorous, pungent and/or corrosive gaseous substances. These gaseous substances comprise, for example, formaldehyde and all other odorous gases such as exhumation-floaters-gangrenous and other putrefactive gases, which are present during an embalming or autopsy.

It should be pointed out that potassium permenganate is an effective oxidation agent which has the capacity to break other substances into simpler and non smelling neutral substances, such as steam and carbonic acid. This function makes the filter portions 17, 18, 51 and 84 effective against gaseous substances such as sulphur compounds, ethylene, ammonia, and formaldehyde.

Consequently, when the above defined foul air comes in contact with the pellets of filtering material while passing through the filter portions 17 and 18, 51 or 84 it is purified very efficiently, as the above defined gaseous substances are removed from the air.

Of course, the efficiency of the filter portions is governed by parameters such as the quality of the filtering material, the size of the pellets, the thickness of the layer of pellets, the air speed through the filter portions, and extreme conditions of humidity or temperature.

The activated pellets of aluminium oxide impregnated with potassium permanganate are originally of a light lilac colour. During use thereof, the pellets change color. It is therefore easy to observe the speed at which the filtering material is consumed. The penetration depth can be observed by taking out a few pellets and breaking them against a hard surface. When the change of color has reached all the way into the core of the pellet, the filtering material has been used up and should be changed. the consumed pellet is inert and can be used as, for example, filling. The advantage is ude to the fact that sorbed pollution has been broken up and dispersed.

If the operational conditions are always constant, the change of filling material can in future be done routinely at the same interval as was measured at the beginning, or perhaps at a shorter interval as a safety margin.

As the ultraviolet ray or the additional filter 89 kills all germs and bacteria instantly, in addition to the fact that the permanganate is an excellent oxidizing agent, in many instances the recirculated air in the room is in better breathing condition that the ambient air from the outside.

As the scrubber apparatus treats the air into a closed circuit, the use of the scrubber apparatus does not increase the heating or conditioning costs as no heated or cooled air is evacuated to the outside.

The present invention has been hereinabove described with reference to preferred embodiments. However, it should be pointed out that any modification to these preferred embodiments within the scope of the appended claims is not deemed to change the concept and nature of the present invention.

What is claimed is:

1. An air scrubber apparatus for purifying foul air produced during an embalming, an autopsy or the like carried out on a work table disposed in a room for embalming, autopsy or the like, comprising:

a housing positioned above the work table, said housing defining a first compartment provided with a bottom inlet opening means for said foul air, and a second compartment adjacent to said first compartment and provided with outlets to said room which are located at predetermined positions;

first air filter means positioned over said bottom inlet opening means of the first compartment, said first filter means comprising a filtering material including aluminum oxide and potassium permanganate and being designed to allow passage of air through it, said filtering material which includes aluminum oxide and potassium permanganate purifying said foul air upon passage thereof through said first filter means;

air pumping means for moving said foul air towards the interior of said first compartment through said first filter means for the purpose of purifying said foul air, said pumping means comprising means for transferring the purified air from the first compartment to said second compartment in order to return the purified air to said room through said outlets, said predetermined positions of said outlets of the second compartment being selected so as to enable a dispersion of the purified air in said room; and an outer wall structure made at least in part of transparent material, the work table comprising a top surface and said outer wall structure defining between the top surface of said work table and the bottom inlet opening means of said housing a substantially closed volume in order to reduce dispersion into the room of the foul air, said outer wall structure being provided with access means in order to allow access for a user to said substantially closed volume and therefore to said top surface of the work table.

2. The air scrubber apparatus of claim 1, further comprising means for killing germs, bacteria and the like present in said moved foul air.

3. The air scrubber apparatus of claim 2, wherein said killing means comprises an ultraviolet ray tube mounted in said first compartment and/or an ultraviolet ray tube mounted in said second compartment.

4. The air scrubber apparatus of claim 2, in which said killing means comprises second air filter means superposed to said first air filter means.

5. The air scrubber apparatus of claim 1, wherein said filtering material comprises activated pellets of aluminium oxide which are impregnated with potassium permanganate.

6. The air scrubber apparatus of claim 1, wherein said first air filter means comprises two sheets of substantially rigid material mounted parallel to each other, said two sheets being provided with holes therein to allow passage of said moved foul air through them and defining a space between these two sheets which is filled with said filtering material.

7. The air scrubber apparatus of claim 1, wherein said first air filter means have an external drawer-like shape, said first compartment being provided with bottom guides to receive said first air filter means having an external drawer-like shape for the purpose of positioning said first air filter means over said bottom inlet opening means of the first compartment.

8. The air scrubber apparatus of claim 1, wherein said first air filter means comprise a first portion corresponding to a first part of said bottom inlet opening means and a second portion corresponding to a second part of the bottom inlet opening means, said scrubber apparatus comprising means for positioning said first and second portions of the first air filter means over said first and second parts of the bottom inlet opening means, respectively.

9. The air scrubber apparatus of claim 1, in which said first compartment comprises no bottom wall thereby providing said bottom inlet opening means, and wherein said first air filter means has a wall-like structure to constitute a bottom wall of said first compartment.

10. The air scrubber apparatus of claim 1, wherein said second compartment is located on one side of said first compartment, said scrubber apparatus comprising lighting means mounted under said second compartment.

11. The air scrubber apparatus of claim 1, in which said room comprises a ceiling, said scrubber apparatus comprising means for hanging up said housing from the ceiling of said room.

12. The air scrubber apparatus of claim 1, comprising an outer wall structure made at least in part of transparent material, the work table comprising a top surface and said outer wall structure defining between the top surface of said work table and the bottom inlet opening means of said housing a substantially closed volume, said outer wall structure being provided with access means in order to allow access for a user to said substantially closed volume and therefore to said top surface of the work table.

13. The air scrubber apparatus of claim 12, further comprising an inner wall structure also made at least in part of transparent material and located inside said outer wall structure, said inner wall structure defining within the substantially closed volume a first volume in contact with said access means and said top surface, and a second volume in communication with said bottom inlet opening means, said inner wall structure being designed to provide communication between the first and second volumes in the proximity of said top surface of the work table.

14. The air scrubber apparatus of claim 12, in which said outer wall structure comprises a first wall formed at least in part by a panel mounted through hinges, said penel mounted through hinges constituting said access means.

15. The air scrubber apparatus of claim 1, wherein said work table has a longitudinal axis, and wherein said housing has a longitudinal axis substantially parallel to the longitudinal axis of the work table, a first end, and a second end, said housing further comprising an inner wall extending from said first end to said second end of the housing, said inner wall forming a common wall of said first compartment and said second compartment.

16. The air scrubber apparatus of claim 15, wherein said first compartment comprises a first half corresponding to the first end of said housing and a second half corresponding to the second end of said housing, and wherein said air pumping means comprises first air pumping means mounted within said first half of the first compartment, and second air pumping means mounted within said second half of the first compartment, said first pumping means comprising means for transferring a first part of the purified air from the first compartment to the second compartment through said inner wall, and said second pumping means comprising means for transferring a second part of the purified air from said first compartment to said second compartment through said inner wall.

17. An air scrubber apparatus for purifying foul air produced during an embalming, an autopsy or the like carried out on a work table disposed in a room for embalming, autopsy or the like, comprising:

a housing positioned above the work table, said housing defining a first compartment provided with bottom inlet opening means for said foul air, and a second compartment adjacent to said first compartment and provided with outlets to said room which are located at predetermined positions;

first air filter means positioned over said bottom inlet opening means of the first compartment, said first filter means comprising a filtering material including aluminum oxide and potassium permanganate and being designed to allow passage of air through it, said filtering material which includes aluminum oxide and potassium permanganate purifying said foul air upon passage thereof through said first filter means;

air pumping means for moving said foul air towards the interior of said first compartment through said first filter means for the purpose of purifying said foul air, said pumping means comprising means for transferring the purified air from the first compartment to said second compartment in order to return the purified air to said room through said outlets, said predetermined positions of said outlets of the second compartment being selected so as to enable a dispersion of the purified air in said room; and a transparent curtain suspended from said housing to define between the top surface of the work table and said bottom inlet opening means a substantially closed volume in order to reduce dispersion into the room of the foul air, which transparent curtain can be opened to allow access for a user to the top surface of said work table.

* * * * *